United States Patent
Ten Grotenhuis et al.

(10) Patent No.: US 10,261,053 B2
(45) Date of Patent: Apr. 16, 2019

(54) ULTRASOUND INSPECTION

(71) Applicant: Ontario Power Generation, Inc., Toronto (CA)

(72) Inventors: Raymond Ten Grotenhuis, Toronto (CA); Yadav Verma, Toronto (CA); Andrew Hong, Toronto (CA); Alex Sakuta, Toronto (CA)

(73) Assignee: Ontario Power Generation Inc., Toronto, Ontario (CA)

( * ) Notice: Subject to any disclaimer, the term of this patent is extended or adjusted under 35 U.S.C. 154(b) by 113 days.

(21) Appl. No.: 15/105,078

(22) PCT Filed: Dec. 17, 2014

(86) PCT No.: PCT/CA2014/051232
§ 371 (c)(1),
(2) Date: Jun. 16, 2016

(87) PCT Pub. No.: WO2015/089667
PCT Pub. Date: Jun. 25, 2015

(65) Prior Publication Data
US 2016/0327520 A1    Nov. 10, 2016

Related U.S. Application Data

(60) Provisional application No. 61/917,066, filed on Dec. 17, 2013.

(51) Int. Cl.
*G01N 29/22* (2006.01)
*G01N 29/28* (2006.01)
(Continued)

(52) U.S. Cl.
CPC ....... *G01N 29/0654* (2013.01); *G01N 29/225* (2013.01); *G01N 29/28* (2013.01);
(Continued)

(58) Field of Classification Search
CPC .. G01N 29/0654; G01N 29/225; G01N 29/28; G01N 29/223; G01N 29/265; G01N 29/0645; G01N 29/262
See application file for complete search history.

(56) References Cited

U.S. PATENT DOCUMENTS 3,921,440 A * 11/1975 Toth .................... G01N 29/265
                                                 376/252
4,331,034 A *  5/1982 Takeda ................ G01N 29/265
                                                 376/252
(Continued)

*Primary Examiner* — Helen C Kwok
(74) *Attorney, Agent, or Firm* — Calfee, Halter & Griswold, LLP

(57) ABSTRACT

A device and method for performing ultra-sound scanning of a substantially cylindrical object. The device comprises a cuff adapted to fit around a circumference of the object, an ultrasound probe mounted about the inner circumference of the cuff and positioned to scan the circumference of the object, and one or more data connections providing control information for the ultrasound probe and receiving scanning data from the ultrasound probe. The probe includes one or more sensors to determine its orientation or location, and this data is used to control the operation of the device and to process data from the array.

26 Claims, 11 Drawing Sheets

(51) Int. Cl.
*G01N 29/06* (2006.01)
*G21C 17/017* (2006.01)
*G21C 17/06* (2006.01)
*G01S 15/89* (2006.01)
*G01S 7/52* (2006.01)

(52) U.S. Cl.
CPC ........ *G01S 7/52079* (2013.01); *G01S 15/899* (2013.01); *G01S 15/8993* (2013.01); *G01S 15/8997* (2013.01); *G21C 17/017* (2013.01); *G21C 17/06* (2013.01); *G01N 2291/2634* (2013.01)

(56) References Cited

U.S. PATENT DOCUMENTS

| | | | | |
|---|---|---|---|---|
| 4,375,165 A * | 3/1983 | de Sterke | ............ | G01N 29/265 73/622 |
| 4,389,894 A * | 6/1983 | Kajiyama | ............ | G21C 17/017 376/245 |
| 4,760,737 A * | 8/1988 | Kupperman | ........... | G01N 29/11 73/622 |
| 4,807,476 A * | 2/1989 | Cook | ................ | G01N 29/0645 73/620 |
| 4,843,884 A * | 7/1989 | House | .................... | G01N 29/26 73/622 |
| 4,872,130 A * | 10/1989 | Pagano | ............. | G01N 29/0609 702/39 |
| 5,821,418 A * | 10/1998 | Dubois | ................. | F16L 55/103 73/493 |
| 6,148,672 A * | 11/2000 | Cawley | ................ | G01N 29/223 73/622 |
| 6,222,897 B1 * | 4/2001 | Hatley | ................. | G01N 29/223 376/245 |
| 6,497,159 B1 * | 12/2002 | Lavoie | ................... | G01B 17/02 73/661 |
| 7,685,878 B2 * | 3/2010 | Brandstrom | ......... | G01B 21/047 376/249 |
| 7,823,454 B2 * | 11/2010 | MacLauchlan | ...... | G01N 29/265 73/618 |
| 8,146,430 B2 * | 4/2012 | Simmons | ............... | G01N 29/04 73/592 |
| 8,590,383 B2 * | 11/2013 | Brignac | ............... | G01N 29/226 73/640 |
| 9,063,059 B2 * | 6/2015 | Na | ...................... | G01N 29/0645 |
| 9,289,150 B1 * | 3/2016 | Gupta | ..................... | A61B 5/044 |
| 2003/0018260 A1 * | 1/2003 | Erikson | ................ | A61B 8/4483 600/447 |
| 2005/0072237 A1 * | 4/2005 | Paige | ................... | G01N 29/225 73/623 |
| 2009/0003130 A1 * | 1/2009 | Barolak | .............. | E21B 47/0006 367/35 |
| 2009/0038398 A1 * | 2/2009 | Lavoie | ................ | G01N 29/225 73/637 |
| 2012/0053856 A1 * | 3/2012 | Morrison, Jr. | ....... | G01N 29/262 702/39 |
| 2014/0238136 A1 * | 8/2014 | Ten Grotenhuis | | G01N 29/0654 73/592 |
| 2015/0308981 A1 * | 10/2015 | Fisher | ................... | G01N 29/04 73/168 |
| 2017/0219534 A1 * | 8/2017 | Ten Grotenhuis | | G01N 29/0654 |
| 2017/0234838 A1 * | 8/2017 | Ten Grotenhuis | | G01N 29/0654 702/56 |

* cited by examiner

ULTRASOUND INSPECTION

CROSS REFERENCE TO RELATED APPLICATION

The application is the U.S. national phase entry of PCT/CA2014/051232, filed on Dec. 17, 2014, which claims priority from U.S. provisional application No. 61/917,066 filed Dec. 17, 2013, the entire disclosures of which are incorporated by reference herein.

FIELD OF INVENTION

This invention relates to methods and devices for carrying out ultrasound inspection, and for pipe inspections.

BACKGROUND

U.S. Pat. No. 8,301,401 to Morrison, Jr. et al. is directed to an ultrasonic probe for inspecting CANada Deuterium Unranium (CANDU) reactor pipes. The probe uses a couplant such as water to fill a cylindrical cuff which is placed around the pipe circumference. The probe uses an ultrasound element array encircling the entire pipe circumference.

U.S. Pat. No. 7,823,454 to MacLauchlan et al. is directed to an ultrasonic inspection method for modeling wavy or irregular surfaces. The method involves using a scanning medium such as water between an ultrasound element array and the surface being inspected.

International Publication WO 2013/044350 discloses a manipulator used for ultrasound inspection of pipe surfaces. The manipulator comprises a cuff fitted around a pipe circumference having an ultrasound array mounted on a shuttle. The shuttle moves around the cuff, scanning the circumference of the pipe using the Total Focusing Method, a version of the Full Matrix Capture technique for collecting and processing probe data. The reference sets out methods for calibrating equipment and software, scanning the pipe surfaces, and collecting and analyzing the probe data using the Total Focusing Method to reconstruct models of the pipe surfaces. The present disclosure relies upon the teachings of this previous publication and hereby incorporates those teachings by reference.

US App. Pub. 2011/0087444 to Volker (hereinafter the '444 publication) is directed to a "pig" for crawling through the bore of a pipe and performing ultrasound inspection of the inner pipe surface. The reference discloses an algorithm for imaging the pipe surface based on backscatter signals. The '444 publication involves Fermat's principle to determine sound paths with the shortest travel time. The modeling involves first building a grid and determining travel time for each point in the grid. The '444 reference requires scanning a pipe from the inside, where the primary information to be ascertained is 3D information about the inner surface of the pipe. This does not solve than the problem of accurately modeling the inner surface of a pipe using a scanning apparatus positioned on the outer surface.

U.S. Pat. No. 7,685,878 to Brandstrom (hereinafter the '878 patent) relates to a device for rotating a pair of ultrasound transducers around a pipe circumference for pipe weld inspection. It allows the cables and other apparatus extending away from the transducers to remain stationary, extending away in only a single direction. '878 teaches an apparatus which can be mounted on the pipe at the position adjacent the weld and which carries the transducers and rotates those transducers around the pipe, bearing in mind that effective access to the pipe is generally only available from one side of the pipe.

Two transducers are rotated around a circumferential location on a cylindrical body for structural testing of the body, carried on a mounting and drive apparatus including a magnetic attachment which can be manually brought up to a pipe from one side only for fixed connection to the pipe on that side at a position axially spaced from a weld. A collar shaped support for the pair of transducers is formed of a row of separate segments which wrap around the pipe from the one side and is rotated around the axis of the pipe to carry the transducer around the circumferential weld. The segments carry rollers to roll on the surface and are held against the pipe by magnets. The transducers are carried on the support in fixed angular position to track their position but in a manner which allows slight axial or radial movement relative to the pipe.

U.S. Pat. No. 7,412,890 to Johnson (hereinafter the '890 patent) relates to a method and apparatus for detecting cracks in pipe welds comprising flooding a volume adjacent to the outer pipe surface with water, then using phased array ultrasound to scan the pipe surface. The apparatus has a rectangular cavity that has its open bottom surface pressed against the pipe surface and is flooded with water. The ultrasound array is positioned at the top of the cavity. Phased-array data collection methods are used.

U.S. Pat. No. 5,515,298 to Bicz (hereinafter the '298 Patent) relates to an apparatus for performing ultrasound scanning of a fingerprint or other object placed on a concave surface. The apparatus projects ultrasound from an array of transducers through an array of pinholes (one per transducer) and against the concave interior of the surface on which the fingerprint rests. The transducers then derive characteristics of the fingerprint from the reflection and scattering of the spherical waveform produced by the pinhole. The apparatus appears to depend on the known structure of the convexo-concave lens structure of the support on which the fingerprint rests.

U.S. Pat. No. 6,896,171 to Den Boer et al (hereinafter the '171 Patent) relates to an apparatus for performing EMAT (electromagnetic acoustic transducer) scanning of a freshly-made pipe weld while still hot. The apparatus may include an array of EMAT transmitter and receiver coils positioned on a ring structure around the outer surface of the pipe. No post-processing algorithm details are disclosed. The apparatus is described as being able to detect the presence of weld defects, and gives some information as to their size, but neither images, precise locations, nor are any further details of defects discussed in the description.

US App. Pub. No. 2009/0158850 to Alleyne et al (hereinafter the '850 publication) relates to a method and apparatus for inspecting pipes wherein the pig apparatus is inserted into the bore of the pipe. Ultrasound transducers are pressed against the inner walls of the pipe and use guided waves (e.g. Lamb waves) of ultrasound within the material of the pipe wall itself to detect defects. Data collection and processing appears to be based on a full matrix capture technique from which different wave modes may be extracted, although a phased-array data collection technique may also be used.

US App. Pub. No. 2009/0078742 to Pasquali et al. (hereinafter the '742 publication) relates to a method and apparatus for inspecting multi-walled pipes, such as those used for undersea transport of hot or cold fluids. The method involves placing an ultrasound probe against the inner pipe surface and scanning at various intervals as the probe rotates around the inner circumference of the pipe wall. The apparatus is a probe positioned at the end of a rotatable arm, which positions the probe within the pipe and then rotates it about the circumference of the inner wall. The '742 publication also discloses methods of positioning the probe at various angles relative to the pipe surface. However, it appears to only teach the use of probes that are displaced from the weld in the pipe's axial direction, and are angled forward or backward toward the location of the pipe weld.

Additional prior art references include U.S. Pat. No. 7,762,136 to Ume, Ifeanyi C. et al., which teaches ultrasound systems and methods for measuring weld penetration depth in real time and off line, U.S. Pat. No. 7,694,569 to McGrath, Matthew et al. which teaches a phased array ultrasonic water wedge apparatus, U.S. Pat. No. 7,694,564 to Brignac, Jacques L. et al. which teaches a boiler tube inspection probe with centering mechanism and method of operating the same, U.S. Pat. No. 6,935,178 to Prause, Reinhard which teaches a device for inspecting pipes using ultrasound, U.S. Pat. No. 6,734,604 to Butler, John V. et al. which teaches a multimode synthesized beam transduction apparatus, U.S. Pat. No. 4,872,130 to Pagano, Dominick A., which teaches an automated in-line pipe inspection system JP 2004028937 to Furukawa, T. et al., which teaches a method for measuring the shape of a welded pipe.

SUMMARY OF THE INVENTION

Example embodiments described in this document relate to methods and devices for performing ultrasound inspection of objects using full matrix data capture techniques.

In a first aspect, the application is directed to a device for performing ultrasound scanning of a conduit, comprising a cylindrical cuff adapted to fit around a circumference of the conduit, an ultrasound probe mounted on the cuff and positioned to scan the circumference of the conduit, and one or more sensors mounted on the cuff to determine the acceleration or orientation of the cuff.

In another aspect, the application is directed to a method for performing ultrasound scanning of a conduit, comprising providing an ultrasound array having a plurality of ultrasound elements arrayed about the circumference of the conduit and at least one sensor providing the acceleration or position of the array, positioning the ultrasound array to project ultrasound signals toward an external surface of the conduit at a first point along the longitudinal axis of the conduit, and performing a full-matrix-capture scan of the first point along the longitudinal axis of the conduit, repositioning the ultrasound array at a second point a along the longitudinal axis of the conduit, performing a full-matrix-capture scan of the second point along the longitudinal axis of the conduit, using data from the at least one sensor to correlate the scan at the first point and the scan at the second point to each other, and repeating the steps of repositioning and performing a full-matrix-capture scan. Each scan comprises transmitting an ultrasound signal from a first ultrasound element in the ultrasound array, sensing and recording ultrasound signals received by each other ultrasound element in the ultrasound array, and repeating the steps of transmitting, sensing and recording. The step of transmitting is performed in turn by each ultrasound element in the ultrasound array other than the first ultrasound element.

Other example embodiments of the present disclosure will be apparent to those of ordinary skill in the art from a review of the following detailed description in conjunction with the drawings.

DESCRIPTION OF EXEMPLARY EMBODIMENTS

Overview

Exemplary embodiments of the invention relate to ultrasound imaging devices and methods for capture and post-processing of ultrasound inspection data.

Figure 1:
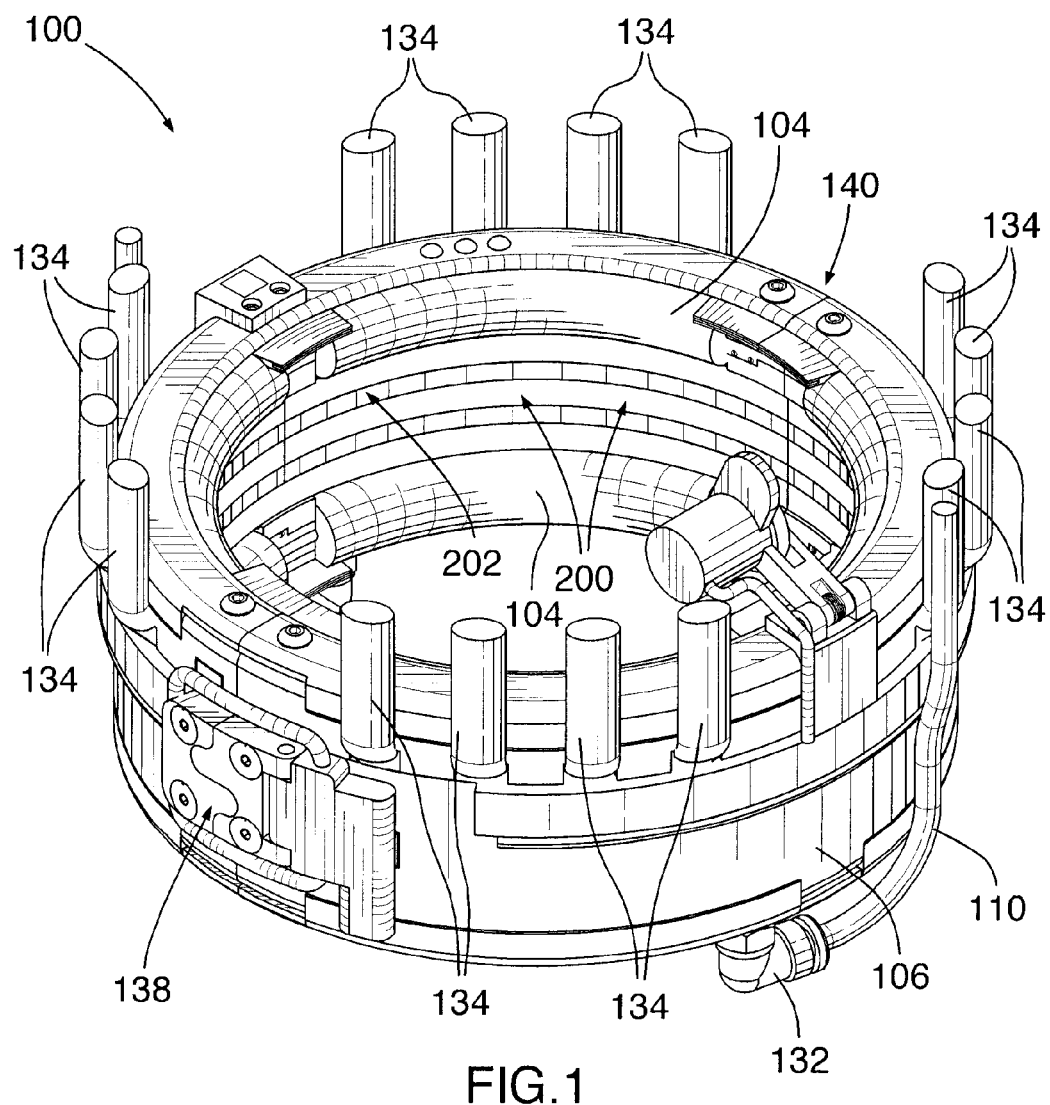
FIG. 1 is a perspective view of an ultrasound probe tool according to an example embodiment, with the data cables cut away and the fluid intake hose removed.

In particular, the described embodiments relate to devices and methods for inspecting pipe welds. With reference to the drawings, FIG. 1 shows an embodiment as a probe tool 100 having a mechanical cuff 106 that fits around a pipe and contains an ultrasound transceiver array 200 encircling the full circumference of the pipe. In the illustrated embodiment the array 200 is composed of four separate elements, each spanning one-fourth of the inner circumference of the cuff's inner surface.

In some embodiments, the array 200 performs multiple transmit-receive cycles of the pipe volume via the Full Matrix Capture data acquisition technique as an operator moves the cuff 106 longitudinally along the length of the pipe. All data from the transmit-receive cycles is retained. The data is then post-processed using a two-step algorithm. First, the outer surface of the pipe is modeled by constructing an intensity map of the surface and filtering this map to detect the boundary of the outer surface. Second, the model of the outer surface constructed during the first step is used as a lens in modeling the inner surface of the pipe, using Fermat's principle. The inner surface is modeled the same way as the outer surface: an intensity map is built, then filtered to detect the boundary.

The mechanical cuff 106 has a cylindrical outer structure having watertight seals 104 on either end for sealing against a pipe surface. In some embodiments, the seals are toroidal seals that roll poloidally, allowing them to maintain contact with the outer surface of the pipe as the cuff 106 moves longitudinally along the pipe surface. The cuff 106 receives a stream of water or another fluid used as an ultrasound scanning medium via a fluid intake 132 and fills the volume between the inner surface of the cuff 106 and the pipe surface with fluid while in operation in order to facilitate ultrasound scanning. In other embodiments, the seals 104 are lip seals formed from a low-friction material such as neoprene, and they simply slide along the pipe surface as the cuff 106 is moved. Various embodiments may use an elastic material for the seals 104 suitable for deforming around irregularities on the outer pipe surface to maintain the watertight seal.

The cuff 106 has an inner ring having on its inner surface a linear array of ultrasound transceiver crystals 202 with the longitudinal axis of the array 200 aligned around the circumference of the cylindrical structure.

In some applications, data is acquired by manually moving the cuff 106 along the longitudinal axis of the pipe while performing multiple transmit-receive cycles with the ultrasound array for each frame. Each frame uses the Full Matrix Capture technique: a single element 202 is pulsed, with each element 202 in the array 200 measuring the response at that position and storing the resulting time-domain signal (A-scan). This process is then repeated, pulsing each element 202 in turn and recording the response at each element 202, resulting in a total data corpus of (N×N) A-scans for an array having N elements 202. In some applications, the stored time period of each A-scan is determined by monitoring for a signal spike past a set threshold (at time t), then retroactively recording all signal data beginning at a set interval before the spike (at time t-C).

Definitions

The following definitions are used within the context of pipe weld inspection as described below.

FMC: Full Matrix Capture. Ultrasonic data collection strategy in which each element in the transducer is individually pulsed while all elements receive. This is repeated for each element in the transducer until all elements have been fired. This strategy creates a data array of n by n where n is the number of elements in the transducer. As a consequence the data files for a FMC inspection is significantly larger than for the equivalent conventional (e.g. phased-array) technique at the same resolution.

Main diagonal: A group of send-receive elements in the data collected using FMC where each transmitting element is its own receiver. The main diagonal view of the FMC data set is identical to the conventional linear electronic B scan. The main diagonal view is the default view of the FMC data B scan.

Matrix: Data structure created when using the FMC data collection strategy. If the columns of the matrix are assigned to identify the transmitting element, then the rows of the matrix correspond to the receiving elements. Each element of the array then corresponds to an A scan related to that transmitter receiver pair. For example: a combination of transmitting on element 17, receiving on element 32 would produce an A scan that would be located under the 17th column on the 32nd row of the FMC data matrix.

TFM: Total Focus Method. Generic name for a variety of automated data analysis strategies that use the data created via the FMC method. TFM relies on summing up the amplitude values in a range of time indices in A scans from various transmitter-receiver combinations. Where valid surfaces exist, the amplitudes constructively interfere to image the surface. Where no such surface exists, the amplitudes destructively interfere forming no image. TFM is also described as being equivalent to focused phased array throughout the entire inspection volume.

Abbreviations and Acronyms

The following abbreviations and acronyms may be used within the context of pipe weld inspection as described below.

| | |
|---|---|
| A Scan | Time-Amplitude plot for a specific Tx-Rx pair |
| DP | Digitization Point - point along the time axis of the A scan |
| feeder | Pipe carrying heavy water coolant to or from the individual fuel channels |
| FMC | Full Matrix Capture |
| Inspection Array | Multi element transducer used for FMC data collection |
| ID | Inside Diameter |
| OD | Outside Diameter |
| TFM | Total Focus Method |
| UT | Ultrasonic Testing |
| WPIT | Weld Profile Inspection Tool |

Position and Orientation Tracking

The position and orientation of the probe tool 100 on the pipe is assessed using a position and orientation detector having a 3-axis gyroscope and a 3-axis accelerometer. The position and orientation data is used to integrate the scanning data from different frames and slices. It is also used to regulate the controls for the ultrasound array, such as varying the sampling rate based on the speed with which the probe tool is moving along the pipe surface. It can differentially regulate the sampling speed for different points on the ultrasound array if they are moving at different rates relative to the pipe surface: for example, when the cuff 106 is being moved around an elbow joint of the pipe, the sampling rate can be lowered for the portion of the ultrasound array on the inside of the elbow relative to the portion on the outside of the elbow, thereby preventing the pipe surfaces on the inside of the elbow from being oversampled.

Figure 6:
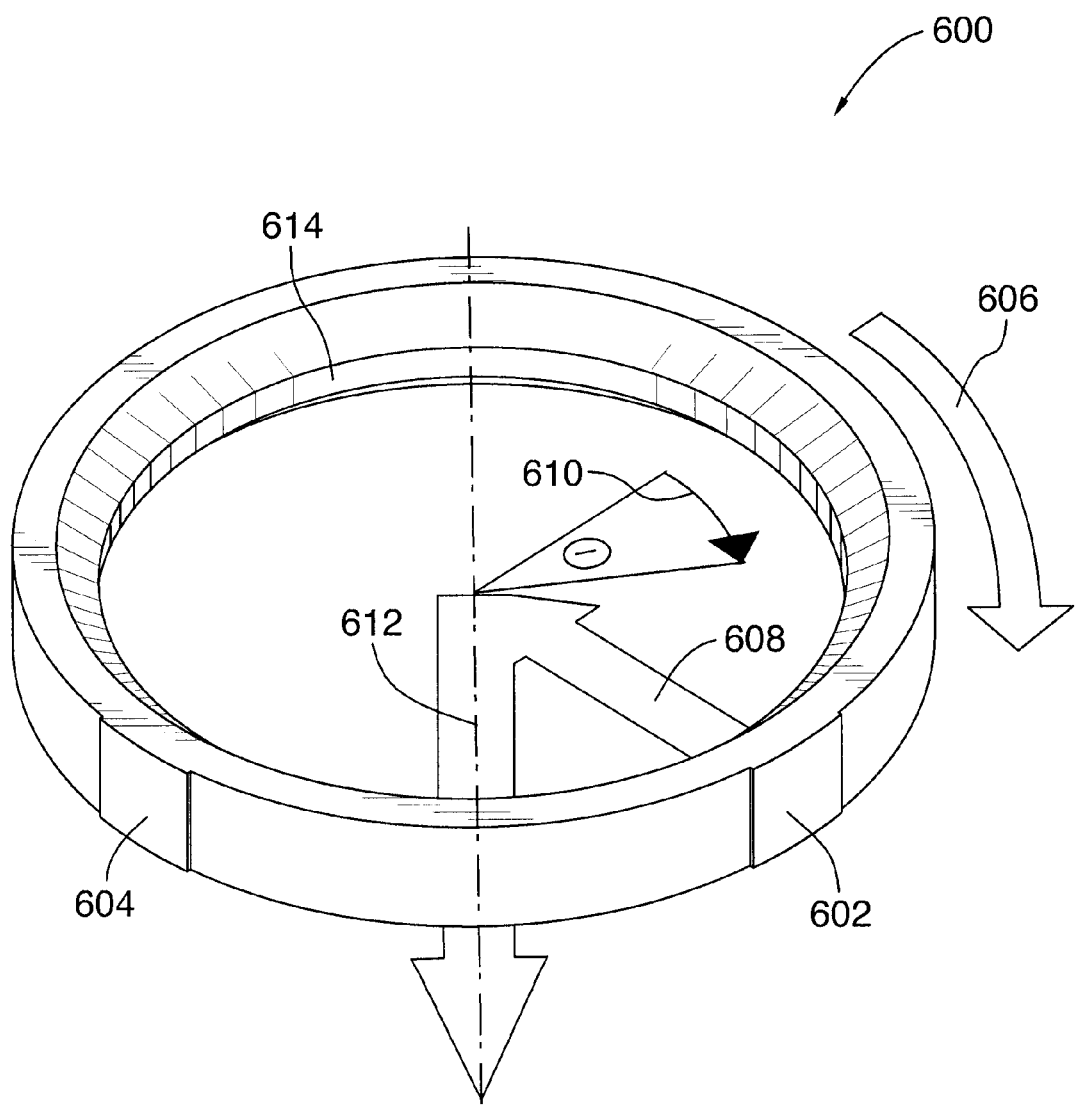
FIG. 6 is an isometric view of a simplified torus shape showing the placement of inertial measurement units on an example toroidal probe tool.

The following describes a method of determining the orientation and position of the probe tool 100 in 3D space. The tool may in some environments undergo several changes in orientation as it is slid along its inspection path. To prevent the oversampling of ultrasound data on the intrados of feeder pipe bends, it may be necessary to know both the position and the orientation of the tool along its path. The described method uses two inertial measurement units (IMUs) working in tandem to determine the position and orientation of the probe tool. With reference to the drawings, FIG. 6 shows an example embodiment of the tool 600 fitted with two IMUs (inertial measurement units) 602, 604 at set positions.

After calibrating the device, a first IMU 602 will record tool orientation using the gravity vector 612. A second IMU 604 is useful when determining tool position on problematic geometry, such as vertical pipe. An encoder and the accelerometer on the second IMU unit 604 may be used to determine the distance the tool has traveled along the pipe. This combination of orientation and axial position will allow for real-time reconstruction of the tool's path through space, for example by detecting the rotation vector 606 through an angle 610 and the acceleration 608 vector.

Figure 7:
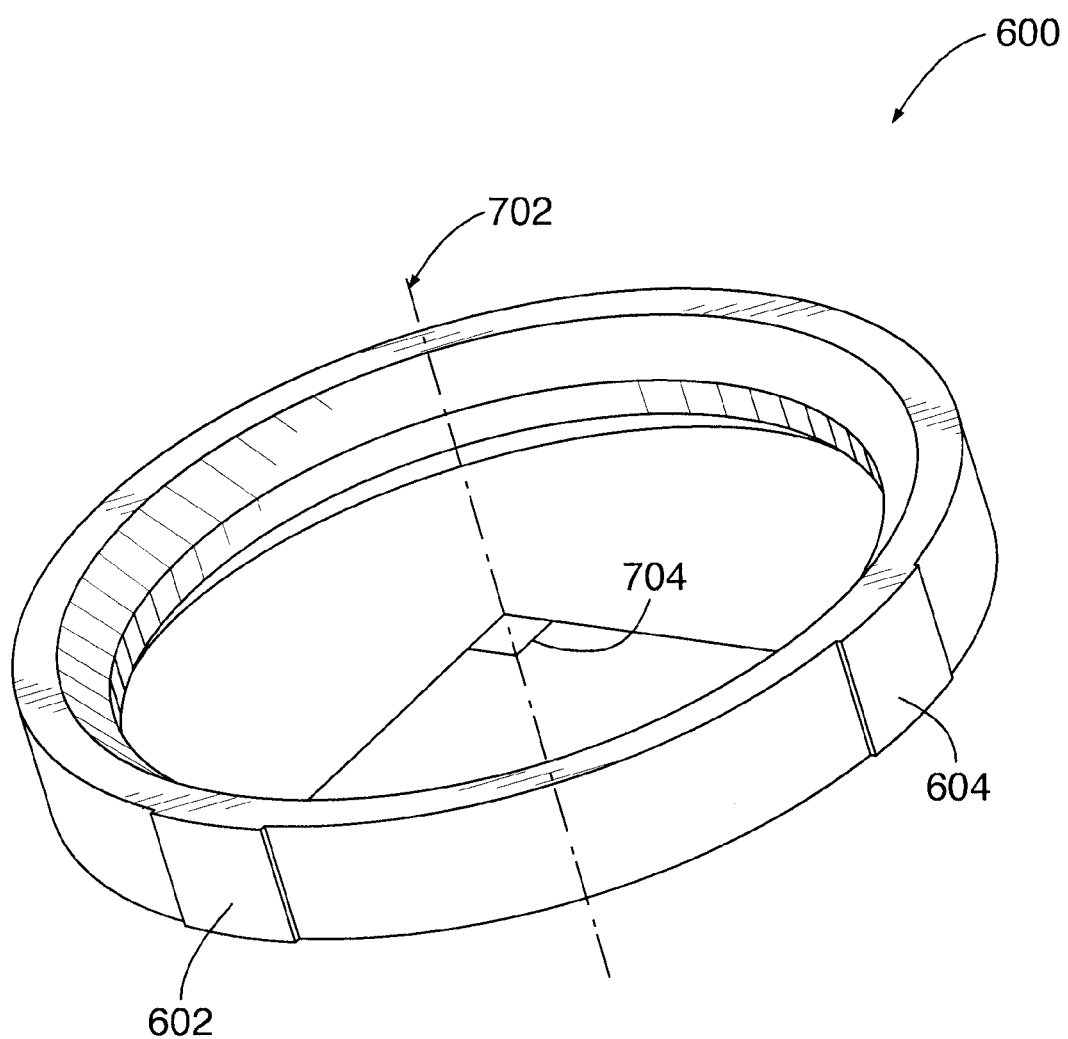
FIG. 7 is a second isometric view of a simplified torus shape showing the placement of inertial measurement units on an example toroidal probe tool.

In the example embodiment shown in FIG. 7, the first IMU 602 and second IMU 604 are placed at points on the circumference of the tool 600 separated by a 90 degree angle 704. They are both oriented with respect to the longitudinal operational axis 702 of the tool 600.

Recording the Orientation of the Tool Using the Gravity Vector

The orientation of the tool 100 will be determined by combining the input from the accelerometer and the gyroscope of the first IMU 602. Readings will be taken when the tool is first initialized, and at the end of each subsequent time interval (t=0, t=1 . . . t=n):

$$\vec{a}(t) = \begin{bmatrix} a_x \\ a_y \\ a_z \end{bmatrix}$$

$$\vec{g}(t) = \begin{bmatrix} g_x \\ g_y \\ g_z \end{bmatrix}$$

$$\vec{O}(t) = \begin{bmatrix} O_x \\ O_y \\ O_z \end{bmatrix}$$

where $\vec{a}(t)$=acceleration vector: orientation of gravity force vector as given by accelerometer $\vec{g}(t)$=gyroscope vector: orientation of tool as given by gyroscope $\vec{O}(t)$=orientation vector: "best guess" as to current orientation of the tool The components of the accelerometer vector are taken directly from the accelerometer readings during each sampling period. The vector is normalized to yield its orientation:

$$\hat{a}(t) = \frac{\vec{a}(t)}{\|\vec{a}(t)\|}$$

From the gyroscope, the angle $\vec{\theta}(t)$ through which the tool has moved over the time interval can be found with:

$$\theta_{xy,avg}(t) = \theta_{xy}(t-1) + \left(\frac{d}{dt}\theta_{xy,avg}\right) * T$$

where
$\theta_{xy}(t-1)$=reading from previous time interval $\frac{d}{dt}\theta_{xy,avg}(t)$ = average rate of change of $\theta$ over the time interval T=duration of time interval
Similarly, $$\theta_{xz,avg}(t) = \theta_{xz}(t-1) + \left(\frac{d}{dt}\theta_{xz,avg}\right) * T$$

$$\theta_{yz,avg}(t) = \theta_{yz}(t-1) + \left(\frac{d}{dt}\theta_{yz,avg}\right) * T$$

It is possible to reconstruct the present orientation of the tool, $\vec{g}(t)$, using the previous orientation vector, $\vec{O}(t-1)$, and the vector of angles $\theta(t)$. This is done as follows:

$$\|\vec{g}(t)\| \sqrt{(g_x^2 + g_y^2 + g_z^2)} = 1$$

$$g_x = \frac{g_x}{1} = \frac{g_x}{\sqrt{(g_x^2 + g_y^2 + g_z^2)}}$$

Using trigonometric identities, this can be simplified to:

$$g_x = \frac{\sin(\theta_{xy}(t))}{\sqrt{1 + \cos(\theta_{xy}(t))^2 * \tan(\theta_{xy}(t))^2}}$$

This can be further simplified to:

$$g_x = \frac{1}{\sqrt{1 + \cot(\theta_{xy}(t))^2 * \sec(\theta_{xy}(t))^2}}$$

which uses fewer trigonometric identities than the first expression, and is therefore less computationally expensive.
Similarly, $$g_y = \frac{1}{\sqrt{1 + \cot(\theta_{yz}(t))^2 * \sec(\theta_{yz}(t))^2}}$$

$$g_z = \frac{1}{\sqrt{1 + \cot(\theta_{xz}(t))^2 * \sec(\theta_{xz}(t))^2}}$$

We now have $\vec{a}(t)$ and $\vec{g}(t)$, the orientation of the gravity force vector and the orientation of the tool as given by the gyroscope, respectively. Taken individually, both of these readings may be subject to error over time—the accelerometer from high-amplitude, short duration noise, and the gyroscope from low-amplitude, long duration drift.

To counterbalance these effects, both inputs may be fed into a complementary filter of the form:

$$\vec{O}(t) = x * \vec{a}(t) + (1-x) * \vec{g}(t)$$

where
x=weight goven to accelerometer input
The quantity x reflects the level to which the accelerometer input can be "trusted," and may be determined through experimentation.

Accommodating Vertical Feeders Using Tandem IMUs

The majority of the feeder pipes on a Canada Deuterium Uranium (CANDU) reactor face are vertical within the intended inspection zone (1-1.5 meters from the fitting, such as a Grayloc™ fitting). This may present a challenge for determining the circumferential orientation of the tool 100 (the θ direction in polar coordinates), as the gravity vector will be aligned with the –z axis for a portion of the inspection scan. FIG. 6 shows such an orientation of the probe tool 600.

This means that, for a portion of the scan, $$\frac{d}{dt}\vec{a}(t) = 0$$

and the accelerometer may be unable to provide useful input to the complementary filter. In such a situation, the orientation of the tool 100 would generally be determined only from the input from the gyroscope. As the gyroscope is subject to drift, this could result in "ghost rotations", where the probe tool software believes the tool is rotating about the pipe axis when no rotation is taking place.

As the operator will likely need to rotate the tool as it is moved along these vertical sections, it is necessary to have an accurate picture of the tool's orientation in the θ dimension with time. This will allow the location of flaws to be determined relative to a fixed reference point, such as the Grayloc™ fitting.

One way to accomplish this is by measuring the centripetal acceleration of the tool using the accelerometers. Centripetal acceleration is given by.

$$a_c = \frac{v_t^2}{r}$$

where
 $v_t$=tangential velocity of tool, measured at IMU origin
 r=radius of tool measured at IMU origin
The magnitude of $a_c$ will generally be small (on the order of 0.014

$$\frac{mm}{s^2}$$

for a 2.5" tool rotated at 40 RPM), thus it is determined that two IMUs, working in tandem to corroborate each other's readings, can be used to provide an accurate picture of the tool's position in θ.

How the inputs from the tandem IMUs 602, 604 may be combined determined through experimentation. A combination of a complementary filter and a threshold technique may be used, with exact weights and limits determined through testing.

Recording the Axial Position of the Tool Using Accelerometers and an Encoder

A combination of inputs from a rotary encoder 1001 and the tandem accelerometers may be used to determine the probe tool's 100 axial position along the pipe. A complementary filter may be used to combine the inputs, with the filter weighted heavily toward the encoder input. This is because the rotary wheel is assumed to be in contact with the pipe surface, and can generally be considered more "trustworthy" than the accelerometers, which are subject to high-amplitude noise.

Through experimentation, it may be found necessary to respond to encoder "slips" by creating a condition where the tool momentarily relies on accelerometer input to determine its position.

Operator Feedback

In some embodiments, an LED light system is integrated into the tool 100 to provide the operator with visual feedback based on current tool status. For example, different light patterns may correspond to different tool events, such as a loss of water column, missed scan, or equipment failure. Such feedback may allow the operator to make quick, informed decisions regarding tool placement, scan speed, etc.

Feedback may come from several sources, including the IMU system (tool 100 moving too rapidly) or from the transducers (low water column, missed scan, etc).

Use of Quaternions in Rotation Calculations

Quaternions present a means of representing 3D rotations using vectors, and are used widely in computer graphics applications. Because they do not involve trigonometric functions, they are not subject to the instability encountered when the function approaches a discontinuity)(tan(90°, for example), a feature of Euler angles that gives rise to the phenomenon of gimbal lock. Gimbal lock may in some cases be a major issue because, as discussed above, a large portion of the inspection with the probe tool may take place on vertical pipe, where the gravity vector is roughly aligned with the −z axis. Accordingly, some embodiments of the tool and its scanning software may make use of quaternions in performing the calculations set out above.

Numeric Approximations to Trig Functions

Related issues arise when calculating trigonometric identities, which is a computationally expensive task. Depending on the sampling rate of the IMUs, this could impede the performance of the system in some circumstances. Tabulating trigonometric values, or creating numeric approximations to trigonometric functions, addresses this accordingly.

Use of an Optical Encoder

An optical encoder can be used in some embodiments to monitor the distance traveled in field conditions (accounting for wet, unclean pipe, changes in reflectivity, etc). In such an embodiment, it may be possible to rely entirely on encoder input to determine the axial position of the tool. This would reduce the complexity of the software, as accelerometer input would not need to be considered when determining position.

More Accurate Integration in Determining $$\frac{d}{dt}\theta(t)$$

The method set out above for calculating the angular velocity from gyroscope readings may in some embodiments rely on the trapezoid method of integration, where the angular velocity readings at the beginning and end of a time interval are simply averaged to produce a reading for that interval.

Sampling at a higher rate, and implementing a "more accurate" method of integration, such as Simpson's rule, could yield better results in some circumstances.

Data Acquisition

FMC inspection superimposes a probe trajectory of a cylindrical geometry on the weld configuration. Depending upon the nature of the joint and the placement of the probe tool over the joint, some distortion of the OD and ID signals can occur. Areas where this may occur are the cheek areas of straight to bend geometries or Grayloc™ to bend geometries. A remedy for this is to re-pass the probe tool 100 over the joint with the intent of optimizing the signals in the regions where distortion is experienced.

The probe data may be fully or partially processed in real-time during the scanning operation. This provides an operator with instant feedback on the adequacy of scanned data. Indicators 136 such as LED lights may be fitted to the probe tool 100 to alert an operator instantly of deficiencies in the probe data, allowing the operator to perform a second pass of the pipe length where the deficiency occurred. Such deficiencies may be caused by an operator moving the cuff too quickly or not smoothly enough; a second pass, which may be performed by "painting back" over the problematic region of the pipe, results in satisfactory data due to smoother, slower movement and/or rotation of the cuff 106.

The indicators may also be used to alert the operator to other problems which may affect the quality of the collected data, such as problems with the water flow or the seal around the pipe.

While the invention has been described as a pipe inspection tool and technique, the general principles and algorithms are applicable to ultrasound imaging in a number of different contexts and applications.

Ultrasound Probe Tool Device

With reference to the drawings, FIG. 1 shows an example embodiment comprising an ultrasound probe tool 100. The probe tool 100 comprises a cuff 106 that is fitted around the circumference of a pipe 2 during the scanning process. The center of the cuff 106 is aligned with the longitudinal axis of the pipe. The probe tool 100 uses a linear array 200 of ultrasound probe elements 202 to scan the slice of pipe encompassed by the cuff 106.

In operation, the cuff 106 is fitted around the pipe, with two watertight seals 104 extending from the edges of the cuff 106 to the pipe surface. In the illustrated embodiment the seals 104 are lip seals made from a low-friction material such as neoprene. In operation, the lip seals slide along the surface of the pipe to maintain the watertight seal. In other embodiments, the seals 104 comprise an elastic core, such as a toroidal spring, and an elastic, low-friction coating such as neoprene. Each seal 104 is fitted to the probe tool 100 within a trench running along each outer edge of the cuff 106. As the probe tool 100 is moved longitudinally along the pipe surface, the seals 104 rotate poloidally to stay within the trench while maintaining contact with the pipe surface to maintain a rolling watertight seal.

The interior region defined by the inner surface of the cuff 106, the seals 104, and the outer pipe surface is then filled with water or another fluid suitable for service as an ultrasound scanning medium. In some embodiments, the water is pumped into the interior volume by a hose 110 incorporated into the probe tool 100. The hose 110 is connected to an external water source and/or pump, and feeds into the interior volume of the cuff 106 via a hose intake 132.

One or more data connections 134 connect the probe tool 100 to one or more external data processing systems and/or controllers. These external systems may control the operation of the probe tool 100 and/or collect and process the data gathered by the scanning operation of the probe tool 100. The data connectors 134 serve to communicate ultrasound probe control data and data collected by the probe between the probe array and the external data processing systems and/or controllers. In other embodiments, some or all of these functions may take place within the probe tool 100 itself, for example by means of an embedded controller and/or data storage and processing unit. The data connectors 134 may also incorporate power lines for powering the operation of the data array and/or other powered elements of the tool 100.

Figure 9:
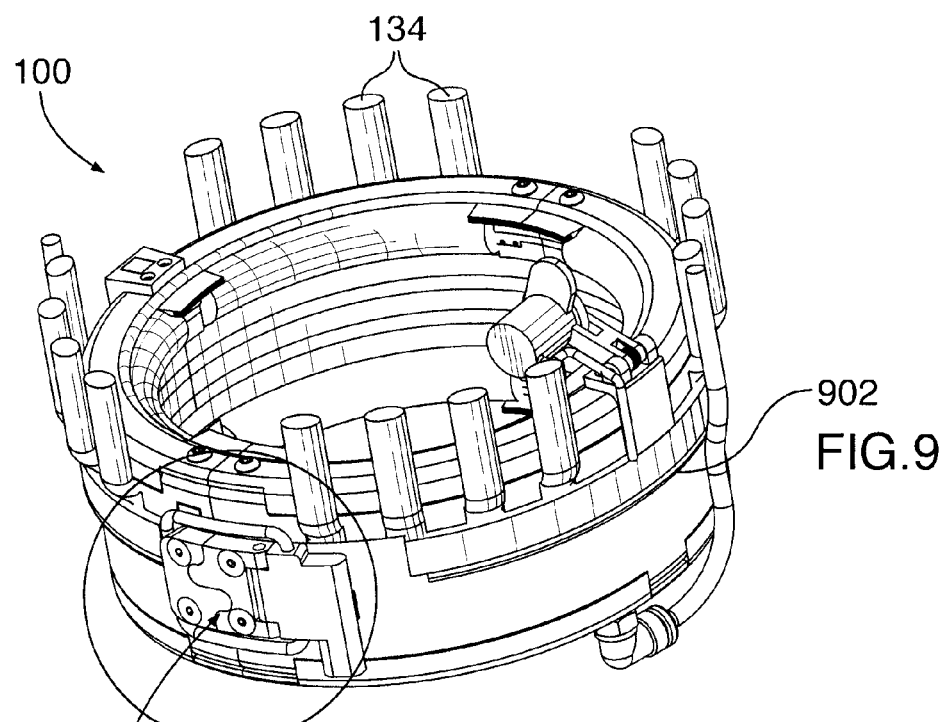
FIG. 9 is a perspective view of an ultrasound probe tool according to an example embodiment, with the data cables cut away and the fluid intake hose removed.
Figure 9A:
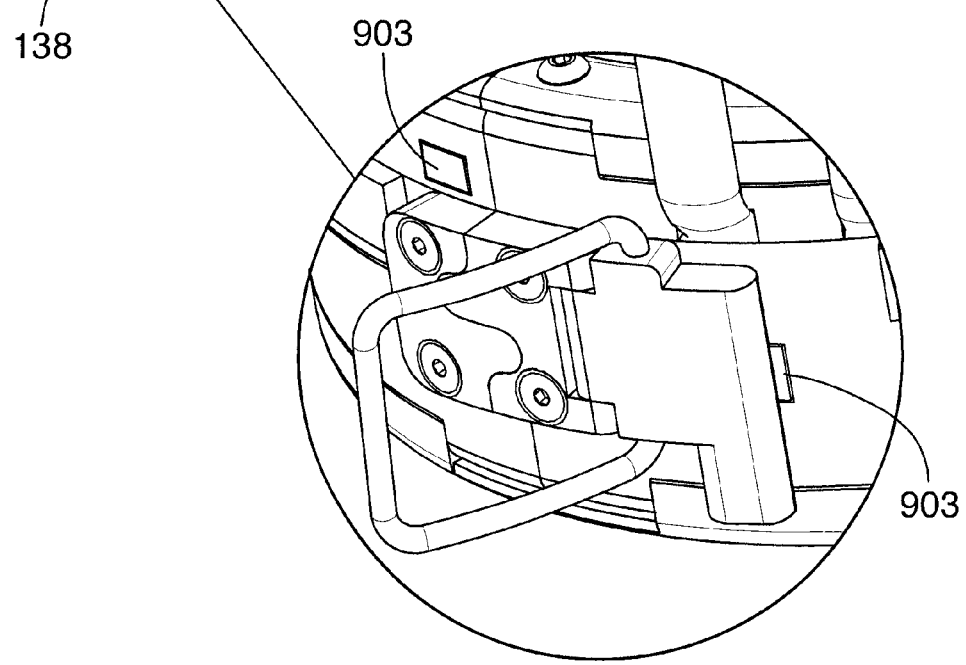
FIG. 9A is a close up of the latch assembly of the ultrasound probe tool according to an example embodiment.

The probe tool 100 may in some embodiments be fitted or removed from a pipe or other scanning subject by means of a hinged design that allows the cuff 106 to be opened. FIG. 1 shows an example embodiment comprising a hinged probe tool, with a hinge 140 allowing the cuff to be opened, and a connector 138 allowing the ends of the cuff to be coupled together into the closed operational position by coupling means such as a latch. The connector 138 is shown in the example embodiment of FIG. 1 as a latch. The latch assembly 901 shown in FIG. 9 provides a further embodiment of the latch mechanism. In some embodiments, such as the one shown in FIG. 10, a hinge assembly 138 allows the cuff 106 to be opened.

Figure 2:
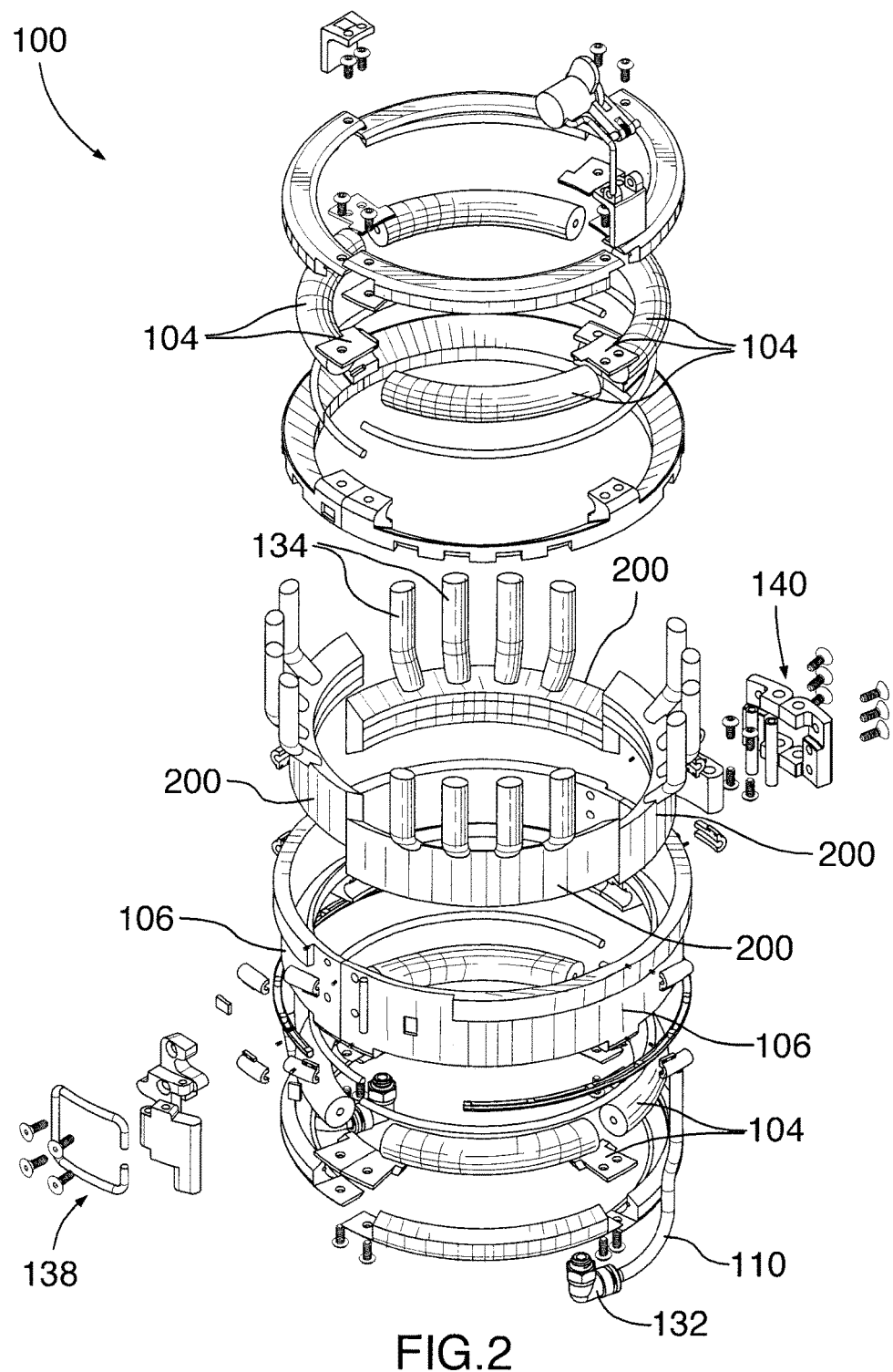
FIG. 2 is an exploded perspective view of the example embodiment of FIG. 1.

FIG. 2 shows an exploded view of the components of the tool of FIG. 1. The seals 104 in this embodiment can be seen to be held in place between outer and inner components of the cuff 106.

Figure 3:
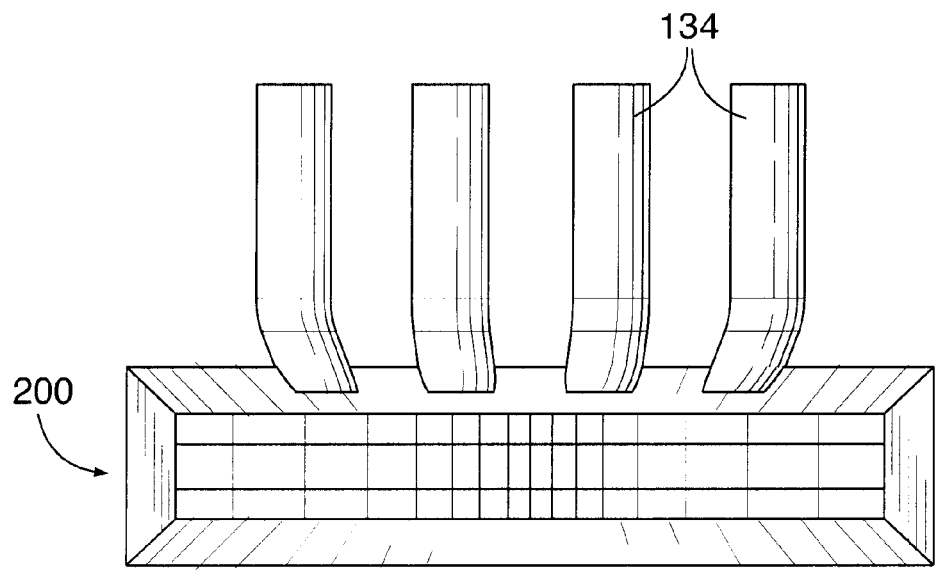
FIG. 3 is a side view of an ultrasound array as used in the example probe tool of FIG. 1.
Figure 4:
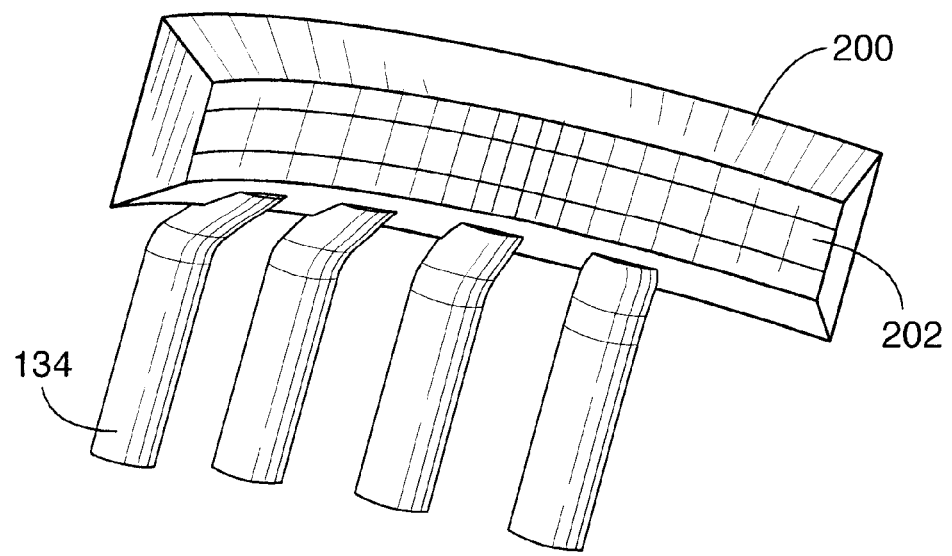
FIG. 4 is a perspective view of the ultrasound array of FIG. 3.
Figure 5:
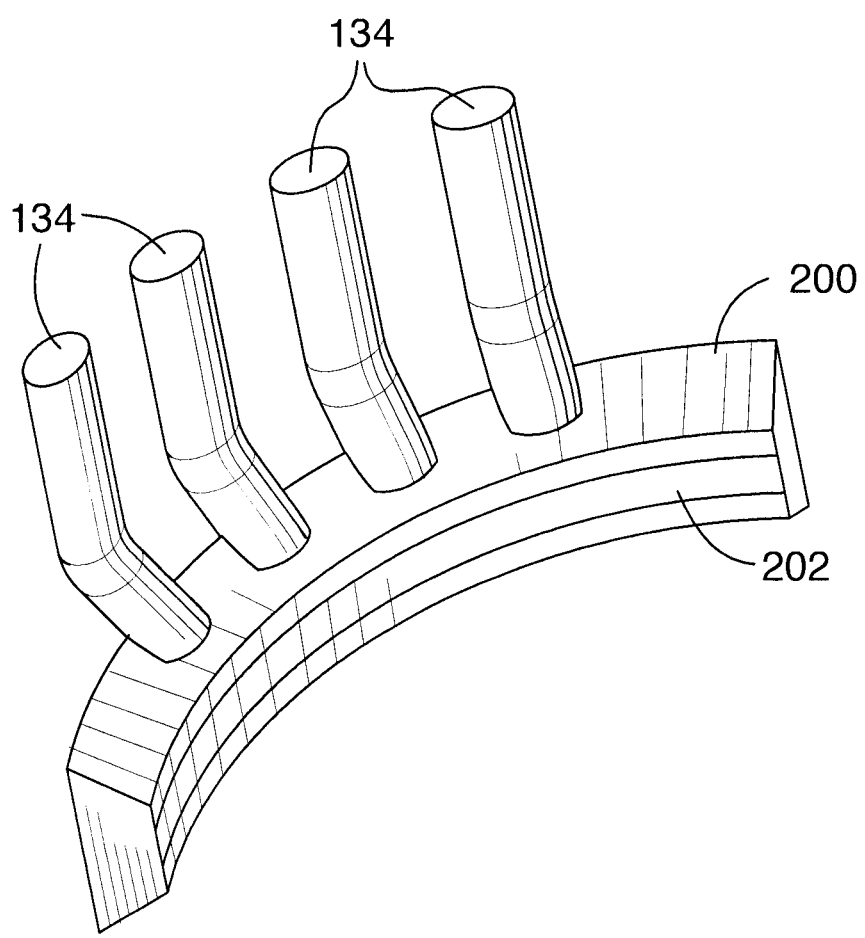
FIG. 5 is a perspective view of the ultrasound array of FIGS. 3 and 4.

The probe tool 100 uses a linear array of ultrasound probe elements, such as resonator crystals, to scan the volume encompassed by the cuff 106. FIG. 3-5 show various views of an example ultrasound array 200. Four of the quarter-circle arrays 200 shown here are placed about the interior circumference of the example probe tool 100 of FIG. 1-2. Some embodiments may join four array segments having 128 elements each to make up a 512-element array. The array 200 has data connectors 134 (shown cut-away here) that power the operation of the array elements 202 and collect data from those elements in operation. In embodiments having a large number of elements, the data connectors 134 may comprise one or more fiber optic data cables or transducer cables 134 capable of carrying at least 250 MB/s.

In operation, the linear array 200 is aligned circumferentially to the longitudinal axis of the pipe being scanned. The pipe is scanned by the full array 200 using the Full Matrix Capture technique described below, then the probe tool 100 is moved along the longitudinal axis of the pipe, after which the scanning process is repeated for the new longitudinal coordinates of the tool's new position. By performing a number of such scans at regularly-spaced intervals along the length of the pipe, a model of the inner and outer surfaces of the circumference of the entire pipe length can be built using the scan data.

Figure 8:
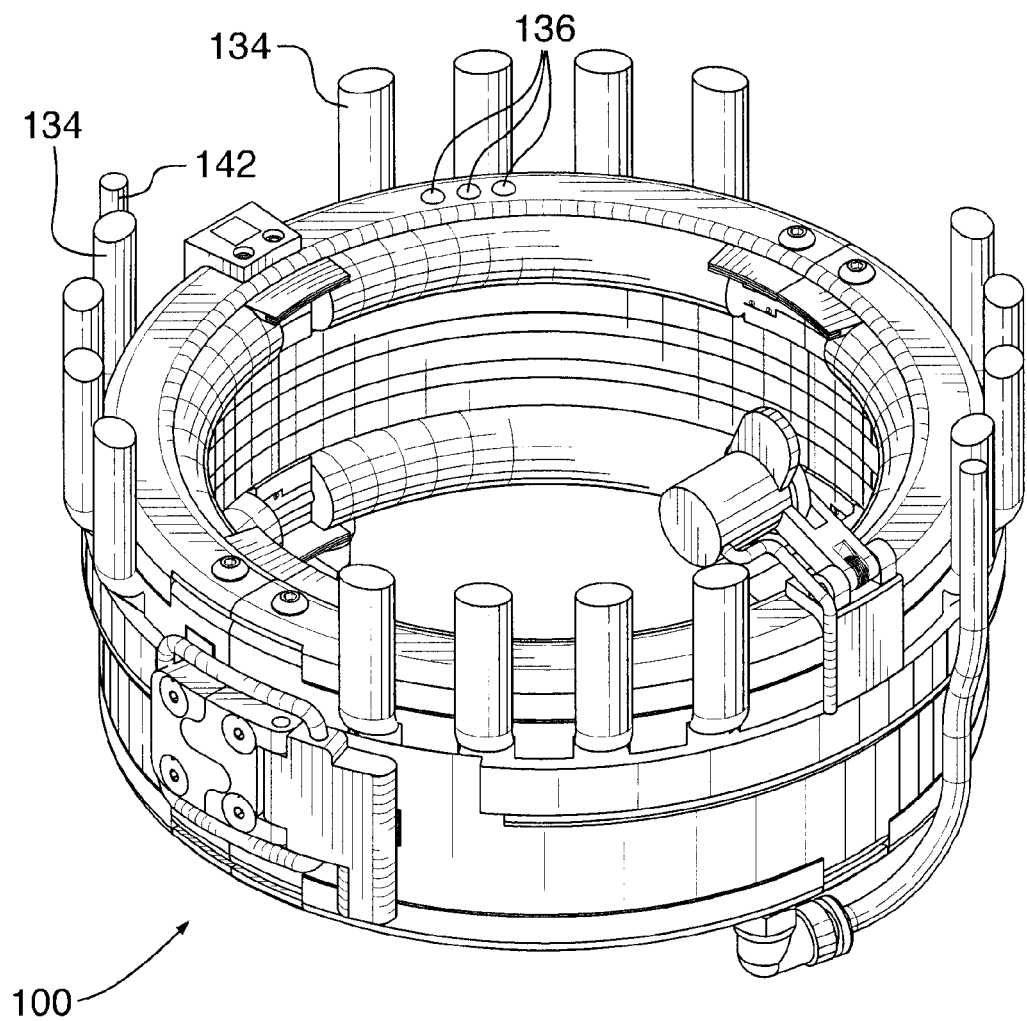
FIG. 8 is an isometric view of an example probe tool having LED indicators on its front face.

In some embodiments, such as the one shown in FIG. 8, the cuff 106 may incorporate one or more indicators 136 to alert an operator to adverse conditions which may need to be addressed before proceeding to scan the next pipe region. In some embodiments, these indicators 136 comprise LED lights attached to the front face of the cuff 106 facing the operator during operation. The indicators 136 receive data from the data connections 134, from an additional indicator data connector 142, and/or internal sensors within the probe tool 100 itself (such as the IMUs). The indicators 136 may alert an operator to problems with the quality of the collected data signal, to problems with the flow of water or the seal around the pipe circumference, or to other problems affecting the quality of the scan. An operator may respond to such an alert by repeating the scan, potentially at a different speed, orientation, and/or direction. The operator may also take steps to correct problems affecting data quality, such as adjusting the seals 104 or checking that the hose 110 is not kinked or obstructed. In some embodiments, such as the one shown in FIG. 9, the ultrasound probe tool 100 comprises one or more LED indicators 902 integrated into the cuff 106 to provide an operator with visual feedback.

In some embodiments, such as the one shown in FIG. 9, one or more hall sensors 903 are mounted on the cuff 106 to determine the acceleration and orientation of the tool. In a further embodiment, such as the one shown in FIG. 10, a rotary encoder 1001 is mounted to the cuff 106 and is used to determine the distance the tool has traveled along the pipe. One or more IMUs 1003 can also be mounted to the cuff 106 and used for recording the device orientation.

Figure 10:
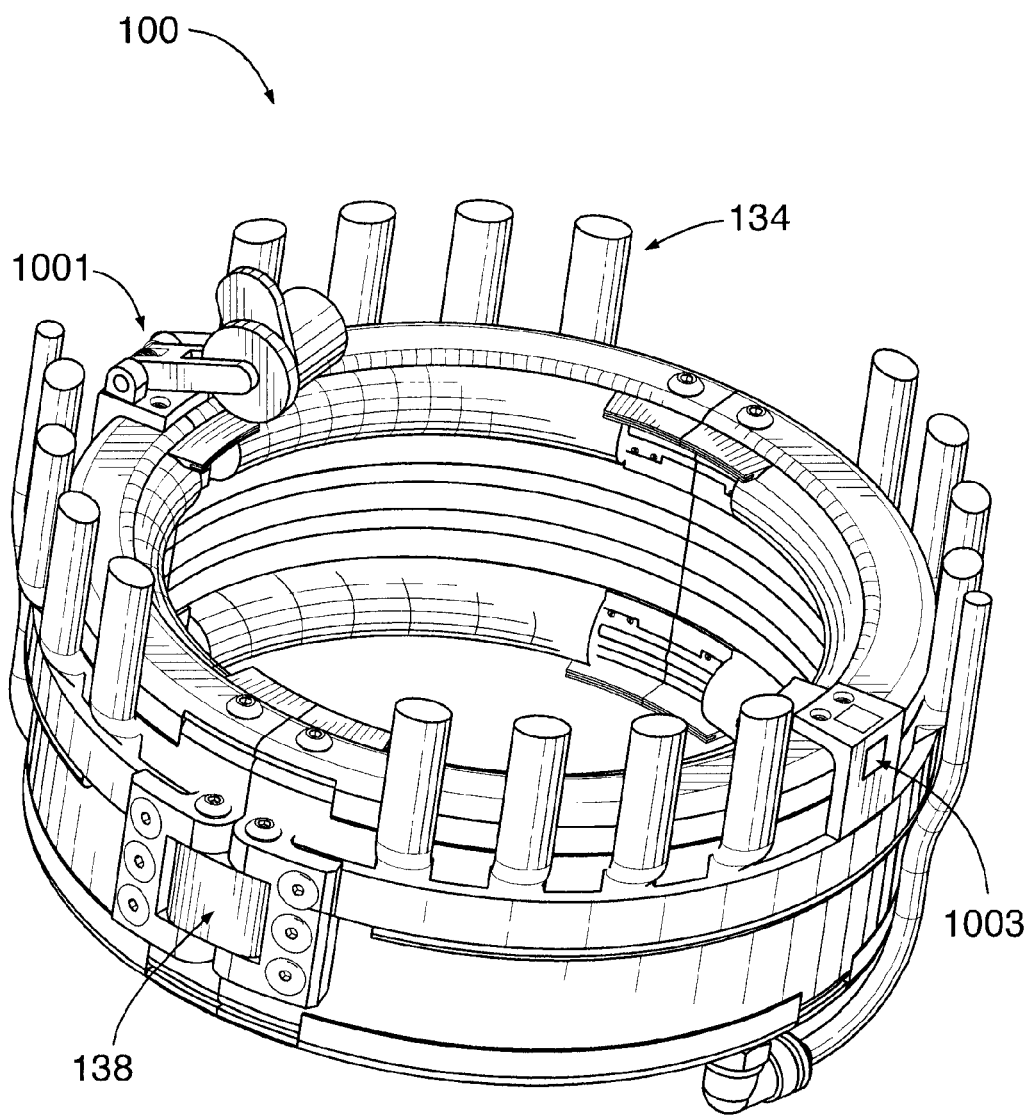
FIG. 10 is a perspective view of an ultrasound probe tool according to an example embodiment.

In some embodiments, as shown in FIG. 9 and FIG. 10, the device comprises a transducer 1104, a transducer cable routing tray 1101, a couplant line 1102, a couplant fitting 1103, a wiper seal 1105, a rolling seal 1106 to maintain a rolling watertight seal, a bearing 1107 and a flex shaft 1108 allowing rotation of the rolling seal 1106.

Figure 11:
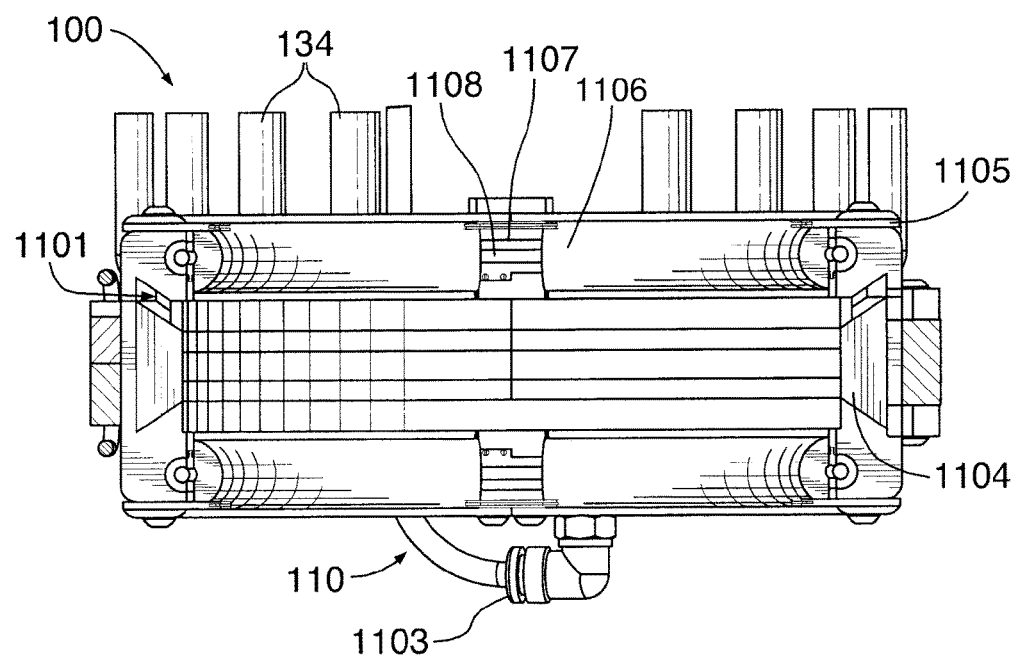
FIG. 11 is a side view of an ultrasound probe tool according to an example embodiment, with the data cables cut away and the fluid intake hose removed.
Figure 12:
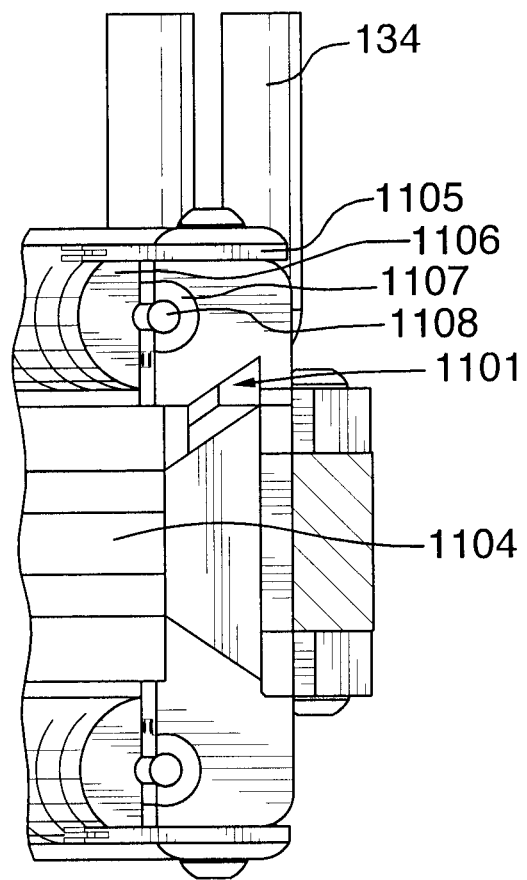
FIG. 12 is an exploded partial side view of an ultrasound probe tool according to an example embodiment.

As shown in FIGS. 11 and 12, the seal at either end of the cuff can be achieved by a rolling seal 1106. The rolling seal is a malleable cylinder which can rotate around a flex shaft 1108 at its axis. The rolling seal itself forms a circle around each end of the cuff. The flex shaft is located within a bearing, also cylindrical, which allows for freedom of rotation of the rolling seal about the flex shaft. A wiper seal 1105 can also be used peripheral to the rolling seal 1106 at either end of the cuff.

Full Matrix Capture (FMC) Data Collection

The Full Matrix Capture (FMC) technique used in some embodiments is a known refinement of the phased-array data capture technique widely used for ultrasound scanning. FMC generally requires capturing a larger volume of data than a comparable phased-array scan, but allows more information to be extracted from a single scan. In Full Matrix Capture, a single element 202 of the ultrasound array 200 is pulsed, transmitting ultrasound energy into the medium being scanned. Each 202 element of the array 200 is used as a receiver for this energy, detecting ultrasound vibrations at its coordinates over the time period following this pulse. This detected vibration is recorded and stored for post-processing. Once the data has been recorded for all n elements 202, a second element is pulsed, and the recording process is repeated for all receiving elements 202. This process then repeats again, with each of the n elements 202 being pulsed in turn and data recorded for each receiving element, resulting in an n by n matrix of recorded data: each receiving element records scan data from the pulse from each transmitting element.

In some embodiments, the data from each receiving element 202 is recorded as a series of digital samples taken over time. The data signal resulting from the pulse of transmitter i captured by receiver j produces a series of m samples taken over the time dimension, resulting in a total three-dimensional matrix of samples n by n by m in size.

In an example embodiment using the probe tool 100 of FIGS. 1 and 2, the operation of the ultrasound array 200 is controlled by an external controller connected to the probe tool 100 by the data connections 134. Data recorded by the array 200 is sent to an external data recorder and processor via the data connections 134, where it is stored and processed as further described below. The controller and data processor may also be in communication with each other, and the recorded data may be used by the controller to calibrate or optimize the operation of the array 200 during scanning.

A single transmit-receive cycle as described above results in n times n A-scans (i.e., time-domain signals received at a receiving element). A single A-scan is generally created by a receiving element by monitoring for vibrations above a set threshold, then recording sensed vibrations and for a set period of time after this threshold is crossed.

Processing of FMC Data

Processing of the captured data may be done concurrently with the scan or afterward. Techniques for processing the captured data may involve application of the Shifting Aperture Focusing Method (SFM), the Interior Focus Method (IFM), and boundary detection and recognition to determine the structure of a scanned object, such as the inner and outer surface contours of a pipe wall. These techniques may allow the detection of subtle variations in pipe thickness, defects in pipe walls, and other structural details of arbitrary inner and outer surfaces of a pipe.

Further details of the TFM technique as applied to pipe inspection are set out in International Publication WO 2013/044350, and in the papers "Volumetric Inspection of Welds Using the Total Focus Method" and "Reconstruction of Phased Array Techniques from the Full Matrix Capture Data Set" presented at the 2012 International Conference on Non-Destructive Evaluation, all three of which are hereby incorporated by reference in full. The WO 2013/044350 reference contains extensive specific details on various topics applicable to or usable in conjunction with the present disclosure: calibration techniques and tools for equipment and software, equipment settings, equipment maintenance, data validation, criteria for signal quality and acceptance of data, storage of probe data, mathematical techniques used in data processing, specifications for equipment and software used to collect and analyze probe data, and detailed data analysis procedures carried out by the software operators. The present disclosure includes refinements of the tools and techniques disclosed in that earlier reference, and incorporates the previous reference in its entirety.

The present disclosure may be embodied in other specific forms without departing from its spirit or essential characteristics. The described embodiments are to be considered in all respects as being only illustrative and not restrictive. The present disclosure intends to cover and embrace all suitable changes in technology.

What is claimed is:

1. A device for performing ultrasound scanning of a conduit, comprising:
   a cylindrical cuff adapted to fit around a circumference of the conduit;
   a full-matrix-capture ultrasound probe mounted on the cuff and positioned to scan the circumference of the conduit; and
   one or more sensors mounted on the cuff to determine at least one of an acceleration of the cuff and an orientation of the cuff;
   wherein the device is configured to vary a sampling rate of the ultrasound probe based on a rate of movement of the device relative to the conduit and using data from said one or more sensors.

2. The device of claim 1, wherein the one or more sensors comprise at least one gyroscope.

3. The device of claim 1, wherein the one or more sensors comprise at least one accelerometer.

4. The device of claim 1, wherein the one or more sensors comprise a gyroscope and an accelerometer operable to determine the orientation and the acceleration of the cuff.

5. The device of claim 4, wherein the gyroscope and the accelerometer are operable to determine orientation and acceleration in three dimensions.

6. A device for performing ultrasound scanning of a conduit, comprising:
   a cylindrical cuff adapted to fit around a circumference of the conduit;
   an ultrasound probe mounted on the cuff and positioned to scan the circumference of the conduit; and
   at least one indicator on the cylindrical cuff for alerting a user of a deficiency in probe data obtained by the ultrasound probe.

7. The device of claim 1, further comprising:
   a seal at either end of the cylindrical cuff for containing fluid in an interior region between an interior surface of the cuff and an exterior of the conduit; and
   a fluid intake for receiving fluid and passing the fluid into the interior region.

8. The device of claim 1, further comprising one or more data connections providing control information for the ultrasound probe and receiving scanning data from the ultrasound probe.

9. The device of claim 1, wherein the ultrasound probe is an array of ultrasound transceivers.

10. The device of claim 9, wherein the array of ultrasound transceivers spans an entire circumference of the conduit.

11. The device of claim 1, wherein the cuff comprises at least two portions detachable from each other for fitting the cuff around the conduit.

12. The device of claim 7, wherein the cuff has at least one indicator for alerting a user of a deficiency in probe data obtained by the ultrasound probe.

13. The device of claim 12, wherein the deficiency is one or more of deficiencies in the probe data which may affect the quality of collected probe data, problems with fluid flow, and problems with the seal around the conduit.

14. The device of claim 3, wherein the accelerometer is a 3-axis accelerometer.

15. The device of claim 1, further comprising:
one or more light indicators for providing an operator with visual feedback.

16. The device of claim 1, further comprising:
a rotary encoder for determining a distance the device has traveled along a pipe;
and one or more inertial measurement units for recording orientation of the device.

17. A device for performing ultrasound scanning of a conduit, comprising:
a cylindrical cuff adapted to fit around a circumference of the conduit;
an ultrasound probe mounted on the cuff and positioned to scan a circumference of the conduit; and
a cylindrical rolling seal at each end of the cylindrical cuff, to maintain a rolling watertight seal.

18. The device of claim 17, further comprising a wiper seal peripheral to said cylindrical rolling seal.

19. The device of claim 17, further comprising a cylindrical shaft extending through an axis of said cylindrical rolling seal.

20. The device of claim 19, wherein said cylindrical shaft is flexible.

21. The device of claim 1, further comprising a processor, wherein the processor is configured to:
perform a full-matrix-capture scan of a first point along a longitudinal axis of the conduit, comprising:
transmitting an ultrasound signal from a first ultrasound element in the ultrasound probe;
sensing and recording ultrasound signals received by the ultrasound elements in the ultrasound probe; and
repeating the steps of transmitting, sensing and recording, wherein the step of transmitting is performed in turn by each ultrasound element in the ultrasound probe other than the first ultrasound element;
reposition the ultrasound probe at a second point along the longitudinal axis of the conduit;
perform a full-matrix-capture scan of the second point along the longitudinal axis of the conduit; and
use data obtained from the one or more sensors in correlating the scan at the first point and the scan at the second point to each other.

22. The device of claim 21, wherein the ultrasound probe has one or more indicators for alerting a user of a deficiency in the probe data, and wherein the processor is further configured to, before performing each full-matrix-capture scan:
transmit at least one ultrasound signal from at least one ultrasound element in the ultrasound probe;
sense at least one ultrasound signal received by at least one ultrasound element in the ultrasound probe;
evaluate a quality of the at least one sensed signal; and
alert the user to an outcome of the evaluation using the at least one or more indicators.

23. The device of claim 21, wherein the ultrasound probe has one or more indicators for alerting a user, and wherein the processor is further configured to, before performing each full-matrix-capture scan:
evaluate whether a position and an orientation of the ultrasound probe are correct based on data from the one or more sensors; and
alert the user to an outcome of the evaluation using the at least one or more indicators.

24. The device of claim 21, wherein the correlating the scan at the first point with the scan at the second point comprises differentially regulating a sampling speed for different points on the ultrasound probe.

25. The device of claim 24, wherein the differentially regulating the sampling speed comprises:
determining if the probe is currently scanning a curved section of the conduit based on data from the one or more sensors; and
sampling with the probe less frequently on an inner side of the curved section than on an outer side of the curved section.

26. The device of claim 6, wherein the at least one indicator is a light indicator.

* * * * *